| United States Patent [19] | [11] | 4,344,940 |
|---|---|---|
| Chow et al. | [45] | Aug. 17, 1982 |

[54] STEROID FORMULATION CONTAINING DIPOTASSIUM EDTA

[75] Inventors: Wing-Sun Chow, Upper Montclair; Donald C. Monkhouse, Princeton, both of N.J.

[73] Assignee: E. R. Squibb & Sons, Inc., Princeton, N.J.

[21] Appl. No.: 325,708

[22] Filed: Nov. 30, 1981

[51] Int. Cl.$^3$ .............................................. A61K 31/58
[52] U.S. Cl. ................................... 424/241; 424/238; 424/243
[58] Field of Search .............................. 424/241, 238

[56] References Cited

U.S. PATENT DOCUMENTS 3,892,856 7/1975 Hill et al. .............................. 424/241
3,892,857 7/1975 Difazio et al. ....................... 424/241

Primary Examiner—Elbert L. Roberts
Attorney, Agent, or Firm—Lawrence S. Levinson; Burton Rodney

[57] ABSTRACT

A steroid formulation is provided which is preferably in the form of a lotion or cream and contains a steroid, such as halcinonide, a polyol vehicle therefor, such as polyethylene glycol, and dipotassium ethylenediaminetetraacetic acid which is soluble in the polyol vehicle and inhibits metal catalyzed degradation of the steroid.

18 Claims, No Drawings

STEROID FORMULATION CONTAINING DIPOTASSIUM EDTA

FIELD OF THE INVENTION

The present invention relates to a steroid formulation, preferably in the form of a lotion, which contains a polyol vehicle and dipotassium ethylenediaminetetraacetic acid which serves as a stabilizer for the steroid and remains in solution in the polyol vehicle upon even prolonged storage.

BACKGROUND OF THE INVENTION

Topical steroid formulations containing 21-chloro-9-fluoro-11β-hydroxy-16α,17-[(1-methylethylidene)bis(oxy)]pregn-4-ene-3,20-dione as the active ingredient are extensively employed in the treatment of skin disorders, such as dermatitis. To be therapeutically effective, the active ingredient must be in a molecular dispersion to facilitate desired percutaneous absorption which is particularly important in achieving a therapeutic response for the management of psoriasis.

The above steroid is insoluble in water (less than 0.0005% soluble) but has been found to have acceptable solubility in certain polyol vehicles, especially polyethylene glycols. However, the steroid is subject to metal catalyzed degradation. Until now, disodium ethylenediaminetetraacetic acid ($Na_2EDTA.2H_2O$) has been employed to inhibit such degradation. However, the $Na_2EDTA.2H_2O$ has only low solubility (less than 0.003%) in the polyol vehicle and EDTA and/or the disodium salt tends to precipitate out of the steroid formulation and reduces product stability.

DESCRIPTION OF THE INVENTION

In accordance with the present invention, it has now been surprisingly found that dipotassium ethylenediaminetetraacetic acid ($K_2EDTA.2H_2O$) is more than 200 times as soluble in the polyol vehicle for the steroid, for example, polyethylene glycol PEG300, as is the corresponding sodium salt. Accordingly, steroid formulations containing the dipotassium salt have excellent stability against metal catalyzed degradation and may be stored for prolonged periods of storage while being free of $K_2EDTA.2H_2O$ and/or EDTA precipitate. Thus, the topical steroid formulation of the invention, preferably in the form of a lotion, is dermatologically beneficial, stable and pharmaceutically acceptable and includes a steroid, a polyol vehicle in which the steroid is soluble, and dipotassium ethylenediaminetetraacetic acid to inhibit metal catalyzed degradation of the steroid.

The active ingredient employed in the formulations of the invention will preferably comprise a steroid such as 21-chloro-9-fluoro-11β-hydroxy-16α,17-[(1-methylethylidene)bis(oxy)]pregn-4-ene-3,20-dione; 9-fluoro-11β,16α,17,21-tetrahydroxypregna-1,4-diene-3,20-dione; 9-fluoro-11β,21-dihydroxy-16α,17-[(1-methylethylidene)bis(oxy)]pregna-1,4-diene-3,20-dione; 21-chloro-9-fluoro-2',3'-dihydro-11β-hydroxy-5'-phenylpregna-1,4-dieno[16α,17-b][1,4]dioxin-3,20-dione acetone solvate or dichloro methane solvate (1:1); progesterone; Δ'-testololactone; 21-(acetyloxy)-9-fluoro-1',2',3',4'-tetrahydro-11β-hydroxypregna-1,4-dieno[1-6α,17-b]naphthalene-3,20-dione, or (11β,16β)-9-fluoro-1',2',3',4'-tetrahydro-11,21-dihydroxypregna-1,4-dieno[16,17-b]-naphthalene-3,20-dione, hydrate 1:1 with 21-chloro-9-fluoro-11β-hydroxy-16α,17-[(1-methylethylidene)bis(oxy)]pregn-4-ene-3,20-dione (halcinonide) being preferred. Other steroids may be employed as well.

The steroid will be present in an amount of from about 0.001 to about 3% by weight, and preferably from about 0.025 to about 0.2% based on the total weight of the composition, depending upon the type of steroid employed and its solubility in the polyol vehicle.

Other active ingredients may be employed in conjunction with the steroid. In such case, the other active ingredients, such as econazole, including the free base and salts thereof, ketoeconazole, miconazole, griseofulvin, nystatin, neomycins, gramicidins, and the like, and mixtures thereof, may be employed in amounts up to and even greater than 3%.

The polyol vehicle employed in the formulations of the invention will preferably comprise a polyethylene glycol vehicle, usually in the form of an aqueous solution containing from about 50 to about 95% by weight of the polyethylene glycol. The polyethylene glycol will have an average molecular weight of within the range of from about 200 to about 600 and preferably from about 250 to about 400.

The polyol will be present in the compositions of the invention in amounts within the range of from about 25 to about 95% by weight and more depending upon the type of pharmaceutical composition, whether it be a lotion, or cream or the like, and the steroid ingredient contained therein.

The dipotassium ethylenediaminetetraacetic acid will be present in an amount within the range of from about 0.001 to about 0.2%, and preferably from about 0.002 to about 0.01% by weight depending upon the type of steroid and polyol vehicle employed. However, regardless of the steroid and polyol vehicle, the $K_2EDTA.2H_2O$ will function to help stabilize the steroid and will remain solubilized in the polyol vehicle for prolonged periods.

The formulation of the invention may also contain an antioxidant such as butylated hydroxytoluene, butylated hydroxyanisole and the like for protecting the active steroid ingredient against oxidation, with butylated hydroxytoluene being preferred. Thus, the present formulation may contain from about 0.001 to about 0.1%, and preferably from about 0.005 to about 0.05% by weight of the antioxidant.

The formulations employing the vehicle in accordance with the present invention may take the form of a lotion, cream or ointment with lotions being preferred.

The lotions and creams of the invention will include the active steroid ingredient "all-in solution" so that substantially no active ingredient crystallizes out at room temperature.

With regard to the lotion formulation of the invention where the steroid is all-in-solution, the lotion will contain from about 0.005 to about 0.6% and preferably from about 0.025 to about 0.2% by weight of the active ingredient based on the weight of the entire lotion formulation, from about 50 to about 95%, preferably from about 85 to about 90% by weight of the polyol, and from about 0.001 to about 0.01%, and preferably from about 0.004 to about 0.01% by weight $K_2EDTA.2H_2O$ based on the weight of the entire lotion formulation, depending upon the solubility of the particular steroid in the particular polyol employed. The active ingredient in the all-in-solution lotion formulation can have part of it also solubilized in the oil phase of the lotion.

The lotion formulation may also contain a glycol type preservative, such as propylene glycol, in an amount within the range of from 50 to about 95% and preferably from about 50 to about 90% by weight of the entire lotion formulation, and/or paraben or other conventional type preservative in an amount ranging from about 0.05 to about 0.5% and purified water in an amount within the range of from about 5 to about 50% by weight and preferably from about 10 to about 50% by weight of the entire lotion formulation.

With regard to the cream formulations of the invention where the steroid is to be all-in-solution, the cream will contain from about 0.005 to about 0.6% and preferably from about 0.025 to about 0.2% by weight of the active ingredient based on the weight of the entire cream formulation, from about 30 to about 70% and preferably from about 40 to about 60% by weight of the polyol, and from about 0.001 to about 0.2% and preferably from about 0.002 to about 0.01% by weight $K_2EDTA.2H_2O$ based on the weight of the entire cream formulation and depending upon the solubility of the particular active ingredient in the particular polyol employed. The all-in-solution cream formulation will include substantially all of the active ingredient in the aqueous polyol phase; however, small amounts of the active ingredient may be present in the oil phase as well. In addition, the all-in-solution cream formulation will also include in the oil phase from about 15 to about 25% and preferably from about 17 to about 23% by weight of the emulsifier-thickener based on the weight of the entire cream formulation, and from about 2 to about 8% and preferably from about 3 to about 5% by weight of oleaginous material or emollient based on the weight of the entire cream formulation. The oil phase of the cream may also optionally include an anti-whitening agent or anti-foaming agent in an amount within the range of from about 0.2 to about 3% and preferably from about 0.5 to about 1.5% by weight based on the entire cream formulation. An antioxidant may also optionally be included in an amount within the range of from about 0.005 to about 0.04% and preferably from about 0.01 to about 0.03% by weight based on the entire cream formulation.

The aqueous phase of the all-in-solution cream formulation may contain a glycol type preservative such as propylene glycol in an amount within the range of from about 5 to about 50% and preferably from about 15 to about 40% by weight of the entire cream formulation and/or a paraben or other conventional type preservative, such as methyl and/or propyl paraben in an amount ranging from about 0.05 to about 0.5%, and purified water in an amount within the range of from about 7 to about 45% by weight and preferably from about 10 to about 40% by weight of the entire cream formulation.

With regard to specific steroid formulations, where 21-chloro-9-fluoro-11$\beta$-hydroxy-16$\alpha$,17-[(1-methylethylidene)bis(oxy)]pregn-4-ene-3,20-dione (halcinonide) is employed in all-in-solution creams or lotions, the polyol vehicle will be preferably employed in an amount within the range of from about 75 to about 95% by weight and more preferably within the range of from about 80 to about 95% by weight, the steroid will be present in amounts ranging from about 0.02 to about 0.2% by weight and the $K_2EDTA.2H_2O$ will be employed in an amount within the range of from about 0.001 to about 0.1% and preferably from about 0.002 to about 0.01% by weight.

Where 9-fluoro-11$\beta$,21-dihydroxy-16$\alpha$,17-[(1-methylethylidenebis(oxy)]pregna-1,4-diene-3,20-dione (triamcinolone acetonide) is employed in all-in-solution creams or lotions, the polyol vehicle will be preferably employed in an amount within the range of from about 75 to about 95% by weight and more preferably within the range of from about 80 to about 95% by weight, the steroid will be employed in amounts ranging from about 0.02 to about 0.2% by weight, and the $K_2EDTA.2H_2O$ will be employed in an amount within the range of from about 0.001 to about 0.1% and preferably from about 0.002 to about 0.01% by weight.

Where other active ingredients (as described above) are employed in a cream or lotion, the polyol vehicle will be preferably employed in amounts within the range of from about 30 to about 65% by weight and preferably from about 40 to about 60% by weight while the active ingredient will vary depending upon its type.

In general, the emulsifier-thickener suitable for use herein may comprise ethers of polyethylene glycol and fatty alcohols, such as, Promulgen, Robinson Wagner Co., which contains some unreacted cetyl and stearyl alcohol, and other non-ionic emulsifying waxes such as Polawax, Croda Co.

The same emulsifier-thickener used in the formulations of the invention may also be obtained by substituting the above-mentioned emulsifying waxes with a mixture of polyoxyethylene (20) stearyl alcohol ether (BRIJ 78, ICI) or polyoxyethylene (20) cetyl alcohol ether (BRIJ 58, ICI) with cetyl or stearyl alcohol. The ratio of the BRIJ or a mixture of the two BRIJ with the fatty alcohol or a mixture of the two alcohols should be within the range of from about 0.6 to about 3.5, preferably from about 1 to about 3.

Another emulsifier system suitable for use in the invention comprises a combination of glyceryl monostearate with polyoxyethylene sorbitan palmitate or stearate and cetyl or stearyl alcohol.

It will also be appreciated that two or more materials may be employed to provide the emulsifying function and the thickening function. Thus, examples of emulsifying agents suitable for use herein include propylene glycol monostearate, as well as the non-ionic polyoxyalkylene derivatives of hexitol anhydride partial long chain fatty acid esters, e.g., the polyoxyalkylene derivatives of sorbitan monolaurate, sorbitan monopalmitate, sorbitan monostearate, sorbitan tristearate, sorbitan monooleate or sorbitan trioleate. These emulsifying agents are commercially available as Tween 20, 21, 40, 60, 65, 80, 81 and 85.

Thickeners suitable for use in combination with the above emulsifying agents include those conveniently employed in topical creams such as, for example, monoglycerides and fatty alcohols, fatty acid esters of alcohols having from about 3 to about 16 carbon atoms. Examples of suitable monoglycerides are glyceryl monostearate and glyceryl monopalmitate. Examples of fatty alcohols are cetyl alcohol and stearyl alcohol. Examples of suitable esters are myristyl stearate and cetyl stearate. The monoglyceride also functions as an auxilliary emulsifier. Other emollients or oleaginous materials which may be employed include petrolatum, glyceryl monooleate, myristyl alcohol and isopropyl palmitate.

The anti-foaming anti-whitening agent increases the elegancy of the cream or lotion and inhibits the formation of a white soapy look upon rubbing the cream or lotion on the skin. An example of such a material suitable for use herein includes silicone fluid.

The preservative suitable for use herein may comprise propylene glycol or parabens (para-hydroxy benzoates) with the propylene glycol being preferred because of less incidence of skin sensitivity.

The following examples illustrate preferred embodiments of the present invention without, however, limiting the same thereto. All temperatures are expressed in degrees Centigrade.

EXAMPLE 1

A liter of halcinonide lotion of the following composition is prepared as described below.

| Ingredient | Amount |
| --- | --- |
| Halcinonide, micronized (average particle size less than 10 microns) | 1 gm/l |
| Polyethylene glycol 300 (90% aqueous solution - 90% PEG) | 900 cc |
| K₂EDTA.2H₂O (0.005% solution in water) | 0.05 gm/l. |
| Butylated hydroxytoluene | 0.5 gm/l. |
| Water q.s. | 1 l. |

Butylated hydroxytoluene was dissolved in the polyethylene glycol with stirring at 25° C. The dipotassium ethylenediaminetetraacetic acid was dissolved in water to form a 0.005% solution. Thereafter, the potassium ethylenediaminetetraacetic acid solution was mixed with the polyethylene glycol containing the butylated hydroxytoluene. Finally the halcinonide powder was mixed into the dipotassium ethylenediaminetetraacetic acid-polyethylene glycol solution at below 35° C. for 30 minutes to form a lotion.

The lotion was found to have excellent stability over prolonged periods of storage (30 months at 25° C.) with no signs of precipitate during such storage.

In a control run, a lotion was prepared as described in Example 1 except that dipotassium ethylenediaminetetraacetic acid was replaced by disodium ethylenediaminetetraacetic acid and the resulting lotion was stored for 14 days at 25° C. during which time a precipitate forms which was identified as ethylenediaminetetraacetic acid.

Thus, it appears that use of the dipotassium ethylenediaminetetraacetic acid in place of the disodium salt in the above lotions markedly and significantly increases the solubility of the ethylenediaminetetraacetic acid in the formulation and increases lotion stability.

EXAMPLE 2

A liter of triamcinolone acetonide lotion having the following composition is prepared as described in Example 1.

| Ingredient | Amount |
| --- | --- |
| Triamcinolone acetonide, micronized | 1 gm/l. |
| Polyethylene glycol 300 (as per Example 1) | 900 cc |
| K₂EDTA.2H₂O (0.005% solution in water) | 0.05 gm/l. |
| Butylated hydroxytoluene | 0.5 gm |
| Water q.s. | 1 l. |

The above lotion is found to have excellent stability upon prolonged storage.

EXAMPLE 3

A halcinonide cream of the following composition is prepared as described below.

| Ingredient | Amount |
| --- | --- |
| Halcinonide, micronized | 0.1 gm |
| Polyethylene glycol 300 (as per Example 1) | 50 gm |
| K₂EDTA.2H₂O | 0.05 gm |
| Cetyl alcohol | 10 gm |
| Myristyl stearate | 10 gm |
| Isopropyl palmitate | 5 gm |
| Water q.s. | 100 gm |

(1) The cetyl alcohol, myristyl stearate and isopropyl palmitate are heated to about 90° C. and melted.

(2) The dipotassium ethylenediaminetetraacetic acid is dissolved in water to form a 0.005% solution which is mixed with the polyethylene glycol.

(3) The halcinonide is dissolved in the polyethylene glycol-dipotassium ethylenediaminetetraacetic acid solution, the water is added and the solution is heated to about 90° C. Thereafter, mixtures (1) and (3) are combined and mixed rapidly at 90° C. to form a cream which is cooled to room temperature.

The above cream is found to have excellent stability even after prolonged storage.

What is claimed is:

1. A pharmaceutical composition comprising a steroid, a polyol vehicle in which said steroid is soluble, and potassium ethylenediaminetetraacetic acid to inhibit metal catalyzed degradation of said steroid.

2. The pharmaceutical composition as defined in claim 1 in the form of a lotion or cream.

3. The pharmaceutical composition as defined in claim 1 wherein the polyol is present in an amount within the range of from about 30 to about 95% by weight and the potassium ethylenediaminetetraacetic acid is present in an amount within the range of from about 0.001 to about 0.2% by weight.

4. The pharmaceutical composition as defined in claim 1 wherein said polyol is polyethylene glycol.

5. The pharmaceutical composition as defined in claim 4 wherein said polyethylene glycol has an average molecular weight of within the range of from about 200 to about 600.

6. The pharmaceutical composition as defined in claim 5 wherein said polyethylene glycol has an average molecular weight of about 300.

7. The pharmaceutical composition as defined in claim 5 wherein said polyethylene glycol is in the form of an aqueous solution containing at least 80% by weight polyethylene glycol.

8. The pharmaceutical composition as defined in claim 1 wherein said steroid is 21-chloro-9-fluoro-11β-hydroxy-16α,17-[(1-methylethylidene)bis(oxy)]pregn-4-ene-3,20-dione; 9-fluoro-11β,16α,17,21-tetrahydroxypregna-1,4-diene-3,20-dione; 9-fluoro-11β,21-dihydroxy-16α,17-[(1-methylethylidene)bis(oxy)]pregna-1,4-diene-3,20-dione; 21-chloro-9-fluoro-2',3'-dihydro-11β-hydroxy-5'-phenylpregna-1,4-dieno[16α,17-b][1,4]dioxin-3,20-dione acetone solvate or dichloro methane solvate (1:1); progesterone; Δ'-testololactone; or 21-(acetyloxy)-9-fluoro-1',2',3',4'-tetrahydro-11β-hydroxypregna-1,4-dieno[16α,17-b]naphthalene-3,20- dione or (11β,16β)-9-fluoro-1',2',3',4'-tetrahydro-11,21-dihydroxypregna-1,4-dieno[16,17-b]-naphthalene-3,20-dione, hydrate 1:1.

9. The pharmaceutical composition as defined in claim 1 wherein said steroid is 21-chloro-9-fluoro-11β-hydroxy-16α,17-[(1-methylethylidene)bis(oxy)]pregn-4-ene-3,20-dione.

10. The pharmaceutical composition as defined in claim 1 in the form of a lotion wherein said potassium ethylenediaminetetraacetic acid is present in an amount within the range of from about 0.001 to about 0.01% by weight and said polyol is polyethylene glycol and is present in an amount within the range of from about 50 to about 95% by weight.

11. The pharmaceutical composition as defined in claim 10 wherein said steroid is 21-chloro-9-fluoro-11β-hydroxy-16α,17-[(1-methylethylidene)bis(oxy)]pregn-4-ene-3,20-dione.

12. The pharmaceutical composition as defined in claim 1 in the form of a lotion wherein said steroid is 21-chloro-9-fluoro-11β-hydroxy-16α,17-[(1-methylethylidene)bis(oxy)]pregn-4-ene-3,20-dione, and said polyol is 80 to 95% aqueous solution of polyethylene glycol having an average molecular weight of about 300.

13. The pharmaceutical composition as defined in claim 1 in the form of a cream wherein said potassium ethylenediaminetetraacetic acid is present in an amount within the range of from about 0.001 to about 0.2% by weight and said polyol is polyethylene glycol present in an amount within the range of from about 30 to about 70% by weight.

14. The pharmaceutical composition as defined in claim 1 further including a preservative.

15. A method of treating dermatitis, which comprises administering topically an effective amount of a composition as defined in claim 1.

16. A method of treating dermatitis, which comprises adminsitering topically an effective amount of a composition as defined in claim 10.

17. A method of treating dermatitis, which comprises administering topically an effective amount of a composition as defined in claim 11.

18. A method of treating dermatitis, which comprises administering topically an effective amount of a composition as defined in claim 12.

* * * * *